United States Patent
Linden et al.

(10) Patent No.: US 9,849,265 B2
(45) Date of Patent: Dec. 26, 2017

(54) METHOD FOR FACILITATING INTRANASAL GUIDANCE

(71) Applicant: JET MEDICAL, INC., Schwenksville, PA (US)

(72) Inventors: Christopher Linden, El Centro, CA (US); Frank Debartola, Roswell, GA (US); Donald Geer, Palm Harbor, FL (US); Kevin E. Sanford, Chalfont, PA (US); Daryl J. Clark, Drexel Hill, PA (US); Timothy M. Schweikert, West Chester, PA (US)

(73) Assignee: JET MEDICAL, INC., Schwenksville, PA (US)

( * ) Notice: Subject to any disclaimer, the term of this patent is extended or adjusted under 35 U.S.C. 154(b) by 0 days.

(21) Appl. No.: 15/412,377

(22) Filed: Jan. 23, 2017

(65) Prior Publication Data

US 2017/0128696 A1    May 11, 2017

Related U.S. Application Data

(62) Division of application No. 14/548,860, filed on Nov. 20, 2014.

(Continued)

(51) Int. Cl.
*A61M 25/00* (2006.01)
*A61M 25/06* (2006.01)
(Continued)

(52) U.S. Cl.
CPC ......... *A61M 25/0041* (2013.01); *A61B 17/24* (2013.01); *A61M 5/007* (2013.01);
(Continued)

(58) Field of Classification Search
None
See application file for complete search history.

(56) References Cited

U.S. PATENT DOCUMENTS 6,228,070 B1    5/2001    Mezzoli
8,388,600 B1    3/2013    Eldredge
(Continued)

FOREIGN PATENT DOCUMENTS

WO    2012/096816 A1    7/2012
WO    2013/119258 A1    8/2013

OTHER PUBLICATIONS

International Search Report and Written Opinion dated Mar. 4, 2015 in International Patent Application No. PCT/US2014/066597 (16 pages).

(Continued)

*Primary Examiner* — Katherine Fernandez
(74) *Attorney, Agent, or Firm* — Fox Rothschild LLP

(57) ABSTRACT

A method for visualization and/or administration of medication of and into the sphenopalatine/pterygopalatine recess of a patient is provided. The method includes providing a sphenocath and inserting a guidewire into the nostril of a patient to a target area proximate the sphenopalatine/pterygopalatine recess of the patient. The sphenocath is advanced over the guidewire and a catheter hub of the sphenocath is rotated relative to a sheath hub to conform to an anatomy of the patient's sphenopalatine/pterygopalatine recess, such that the distal end of the catheter tube is proximal to the target area. The sphenocath is then advanced relative to a sheath assembly so that the distal end of a sphenocath catheter tube extends from a sphenocath sheath tube distal end and bends along the guidewire. The guidewire is removed and contrast media, fluids, and/or medication is administered to the patient's sphenopalatine/pterygopalatine (Continued)

ganglion disposed within the sphenopalatine recess of the patient.

7 Claims, 12 Drawing Sheets

Related U.S. Application Data

(60) Provisional application No. 61/907,328, filed on Nov. 21, 2013.

(51) Int. Cl.
| | | |
|---|---|---|
| *A61B 17/24* | (2006.01) | |
| *A61M 5/00* | (2006.01) | |
| *A61M 5/46* | (2006.01) | |
| *A61M 11/00* | (2006.01) | |
| *A61M 25/01* | (2006.01) | |
| *A61M 25/09* | (2006.01) | |

(52) U.S. Cl.
CPC .............. *A61M 5/46* (2013.01); *A61M 11/00* (2013.01); *A61M 25/0045* (2013.01); *A61M 25/0068* (2013.01); *A61M 25/0097* (2013.01); *A61M 25/0108* (2013.01); *A61M 25/0662* (2013.01); *A61M 25/09* (2013.01); *A61M 2025/0008* (2013.01); *A61M 2025/0046* (2013.01); *A61M 2025/0062* (2013.01); *A61M 2025/0073* (2013.01); *A61M 2025/0681* (2013.01); *A61M 2210/0618* (2013.01); *A61M 2210/0681* (2013.01)

(56) References Cited

U.S. PATENT DOCUMENTS

| | | |
|---|---|---|
| 2005/0281751 A1 | 12/2005 | Levin |
| 2006/0210605 A1 | 9/2006 | Chang et al. |
| 2006/0217655 A1* | 9/2006 | Vitullo ............... A61N 1/36017 604/21 |
| 2006/0276552 A1 | 12/2006 | Barbut et al. |
| 2009/0216196 A1 | 8/2009 | Drontle et al. |
| 2010/0030188 A1 | 2/2010 | Xia |
| 2010/0057048 A1 | 3/2010 | Eldredge |
| 2013/0274600 A1* | 10/2013 | Jenkins ................... A61B 1/07 600/431 |
| 2014/0018732 A1* | 1/2014 | Bagaoisan ........ A61M 25/0147 604/95.04 |

OTHER PUBLICATIONS

U.S. Appl. No. 15/548,860, filed Nov. 20, 2014, System and Method for Facilitating Intranasal Guidance.

\* cited by examiner

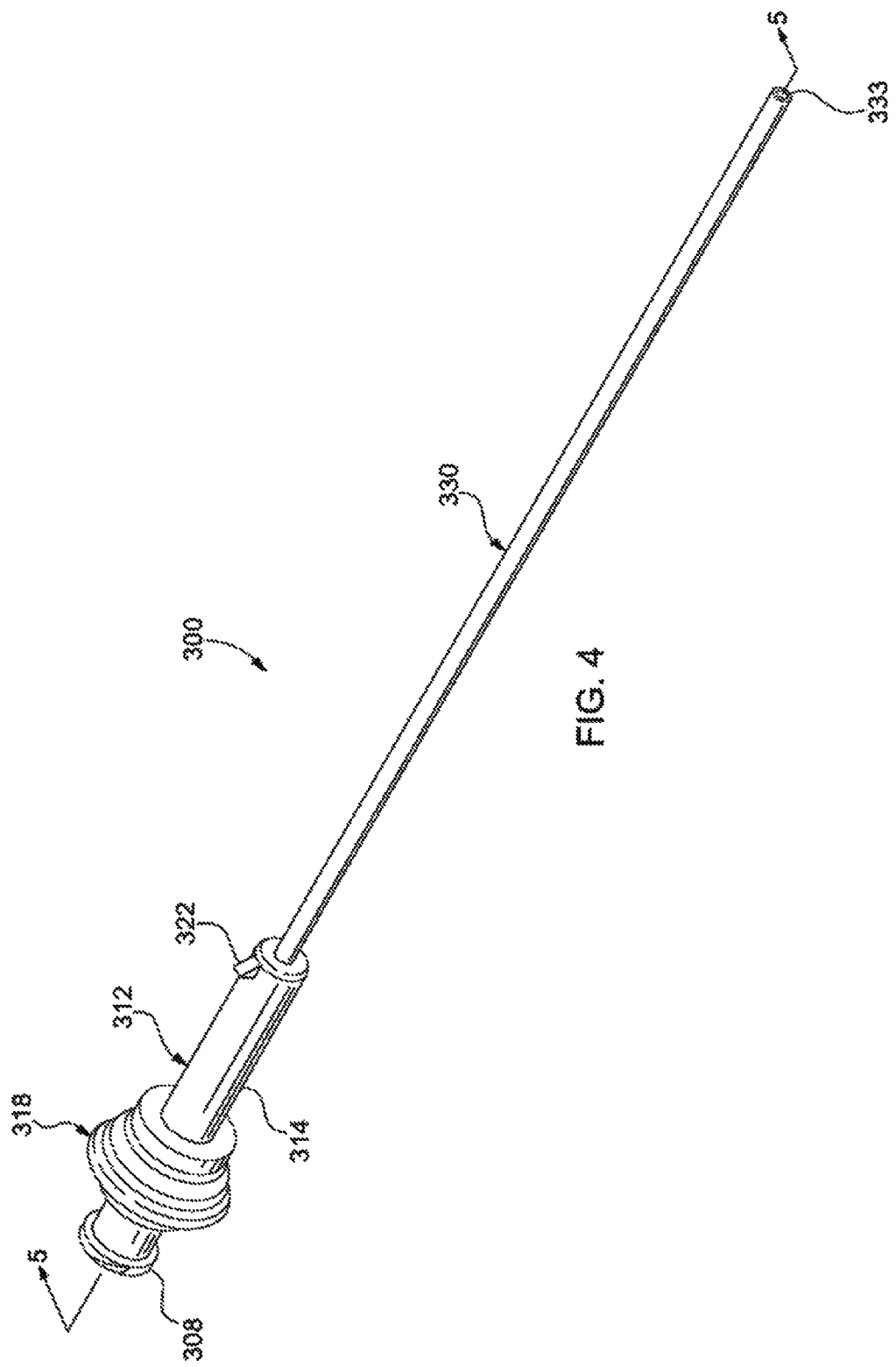

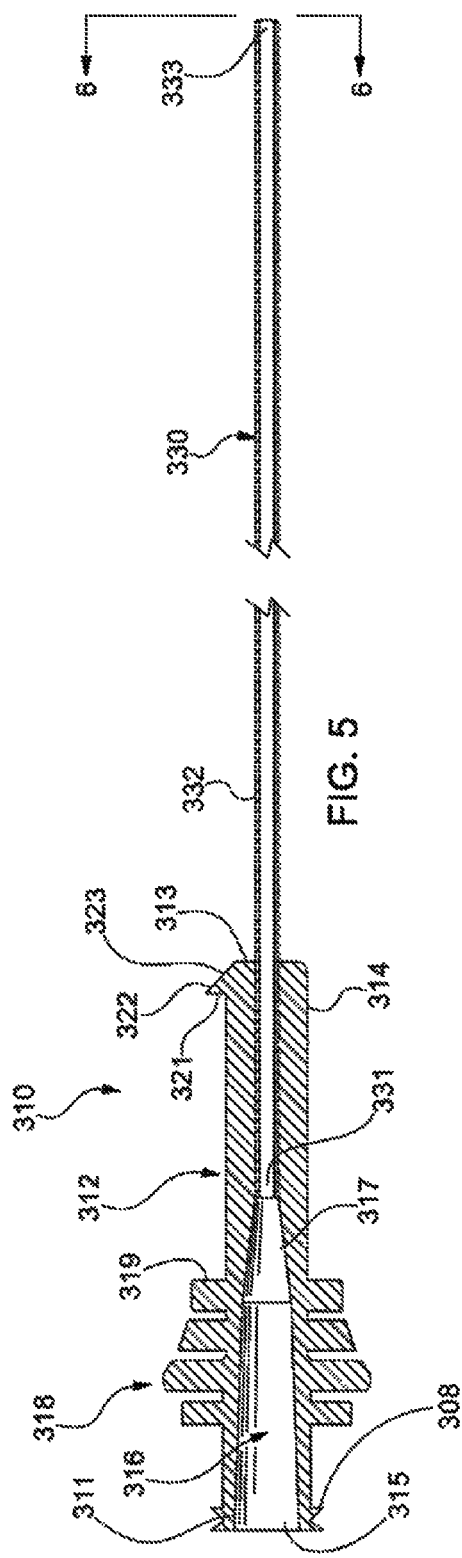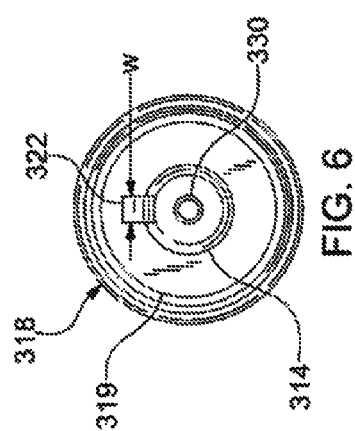

METHOD FOR FACILITATING INTRANASAL GUIDANCE

CROSS REFERENCE TO RELATED APPLICATIONS

This application is a divisional of U.S. patent application Ser. No. 14/548,860, filed on Nov. 20, 2014; which claims the benefit of U.S. provisional patent application serial no. 61/907,328, filed on Nov. 21, 2013, the entireties of which are hereby incorporated by reference.

FIELD OF THE INVENTION

This invention relates to an apparatus and method for facilitating intranasal guidance. More particularly, the invention relates an apparatus and method for positioning the tip of a catheter adjacent to a patient's sphenopalatine/pterygopalatine recess.

BACKGROUND OF THE INVENTION

U.S. Pat. No. 8,388,600, incorporated herein by reference, describes a device and method of positioning a catheter tip within a patient's nasal cavity in order to deliver an anesthetic to create a nerve block. As explained in U.S. Pat. No. 8,388,600, FIG. 1 depicts a cutaway view of the anatomical features of a typical human nasal cavity. One skilled in the art will recognize that certain anatomical features and structures of the human nasal cavity have been omitted to avoid obscuring the structures relevant to the practice of the current invention. To help orient the reader, the mouth 106 is illustrated with teeth 108 and tongue 110. The anatomical structures relevant to the practice of the current invention include the palate 100 which separates the oral cavity 102 from the nasal cavity 104, the inferior sinus turbinate 112, the middle sinus turbinate 114 and the superior sinus turbinate 116 as well as the nasal bone 122. The middle sinus turbinate 114 and superior sinus turbinate 116 define the sphenopalatine/pterygopalatine recess 118. Deep within the sphenopalatine/pterygopalatine recess 118 at the posterior 124 of the sphenopalatine/pterygopalatine recess 118 lies the sphenopalatine/pterygopalatine ganglia 120.

One skilled in the art will recognize that the medical community is not uniform in the terminology with regard to the sphenopalatine or pterygopalatine ganglia. Certain practitioners use sphenopalatine while others use pterygopalatine. Therefore, the present description will refer to the ganglia labeled 120 as the sphenopalatine/pterygopalatine ganglia 120. Similarly, the recess labeled 118 will be referred to as the sphenopalatine/pterygopalatine recess 118. However, this terminology is in no way limiting on the structure for which the present invention is intended. Where practitioners or scientist differentiate between the sphenopalatine ganglia or the pterygopalatine ganglia, the present disclosure will be understood to apply to either structure.

As is evident from FIG. 1, the structure of the nasal cavity makes it difficult to deliver a catheter tip to the sphenopalatine/pterygopalatine recess 118. While U.S. Pat. No. 8,388,600 describes a device and method of positioning a catheter tip, such may not be sufficiently accurate and/or may be complicated in use.

SUMMARY OF THE INVENTION

In at least one aspect, the present invention provides an apparatus, system, and method for facilitating intranasal fluoroscopic guidance, visualization, administration of radiopaque substances, fluids, and medication to a patient's nasal sinus including the sphenopalatine/pterygopalatine recess. The apparatus includes a wire in which the internal catheter tracks over the wire into the desired location, and a catheter having a lumen disposed therethrough, the catheter comprising an intrinsic curvature, soft straight proximal end, or a shape memory curvature with respect to a longitudinal axis of the catheter such that the insertion end of the catheter lies in a first plane and the manipulation end of the catheter lies in a second plane, wherein the catheter smoothly transitions between the wire, the first plane and the second plane, the intrinsic curvature conforming to the wire and the patients nasal anatomy such that the catheter may be inserted into a sphenopalatine/pterygopalatine recess. The external catheter assists the delivery of the catheter by adding stability and pushability to the overall system allowing the internal catheter to be softer and more comfortable to the patient.

In another aspect, the invention provides a sphenocath including a sheath assembly including a sheath hub with a sheath tube extending therefrom with a passage extending from a proximal end of the sheath hub to a distal end of the sheath tube; a catheter assembly including a catheter hub with a catheter tube extending therefrom with a passage extending from a proximal end of the catheter hub to a distal end of the catheter tube; wherein the catheter assembly passes through the sheath assembly with a portion of the catheter hub engaging a portion of the sheath hub to limit relative rotation between the hubs while permitting relative axial movement such that in an initial non-extended position the distal end of the catheter tube is proximate to the distal end of the sheath tube. A system further including a guidewire is also provided.

In yet another aspect, the invention provides a system including a sphenocath configured to be positioned over and guide into position by a guidewire.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 4 is an isometric view of an exemplary catheter assembly of the sphenocath of FIG. 2.

FIG. 5 is a cross-sectional view along the line 5-5 in FIG. 4.

FIG. 6 is an elevation view along the line 6-6 in FIG. 4.

DETAILED DESCRIPTION OF THE INVENTION

Figure 1:
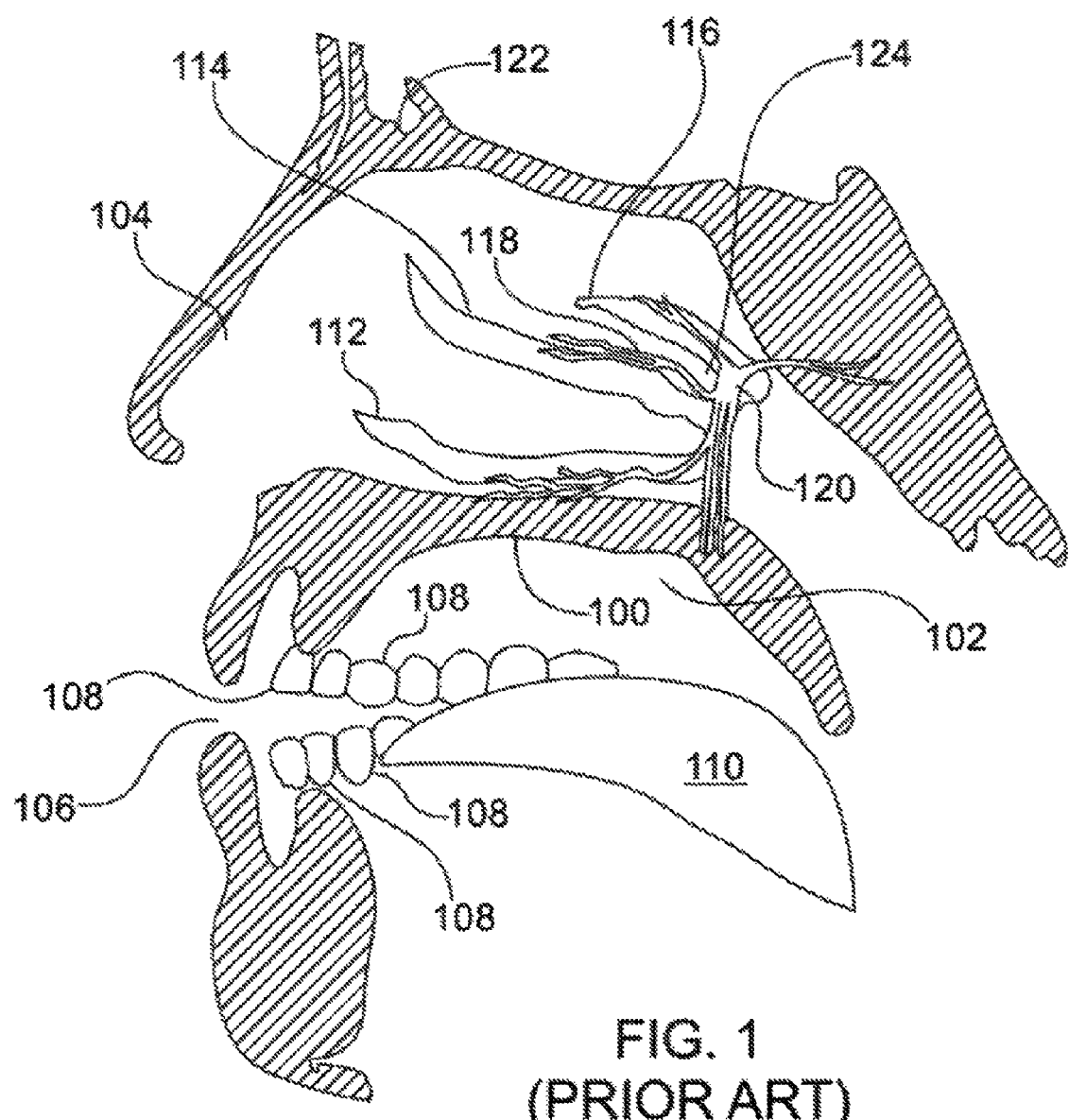
FIG. 1 is a schematic cutaway view of an exemplary facial anatomy of a patient.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Figure 2:
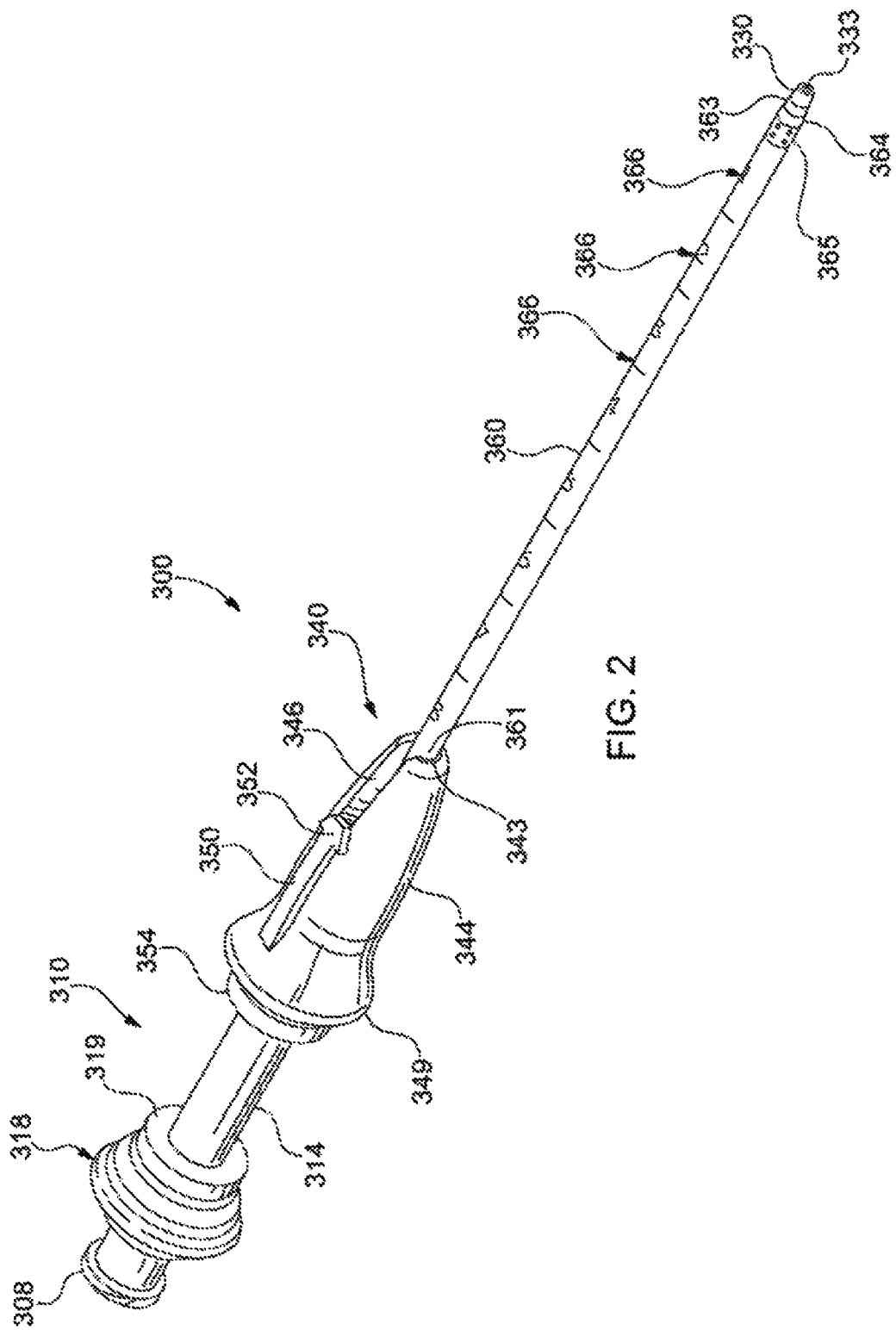
FIG. 2 is a perspective view of a sphenocath in accordance with an exemplary embodiment of the invention in an initial, non-extended position.
Figure 3:
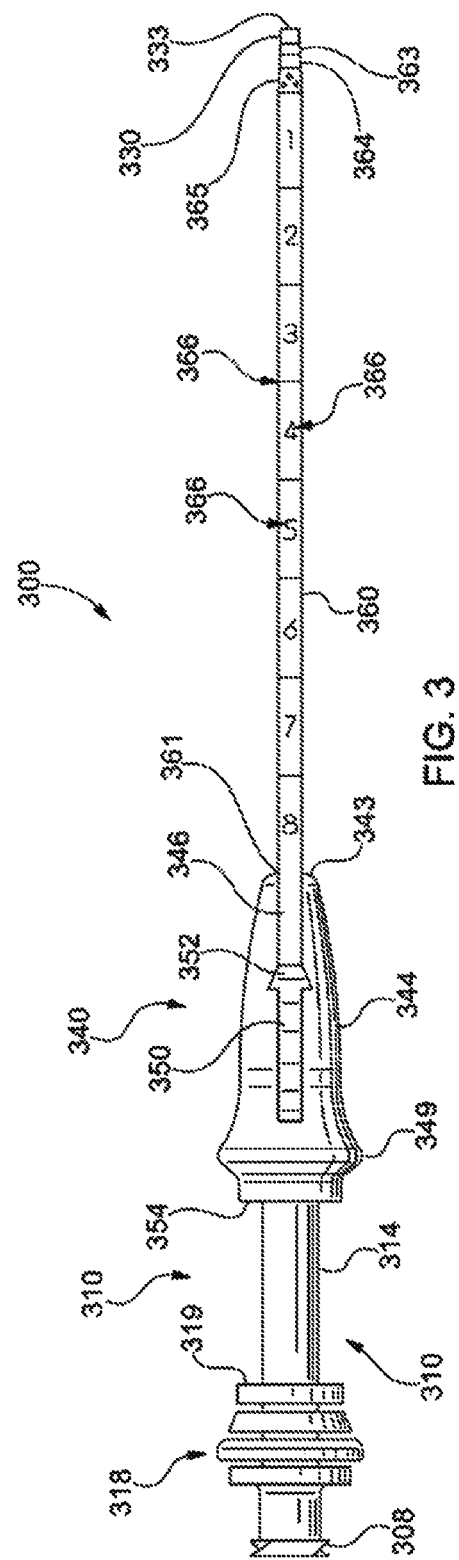
FIG. 3 is a top plan view of the sphenocath of FIG. 2.
Figure 8:
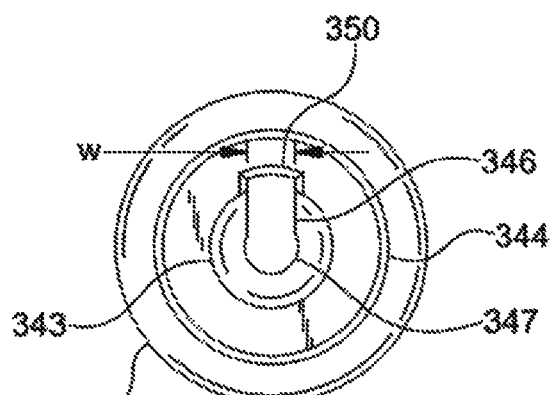
FIG. 8 is an elevation view along the line 8-8 in FIG. 7.
Figure 9:
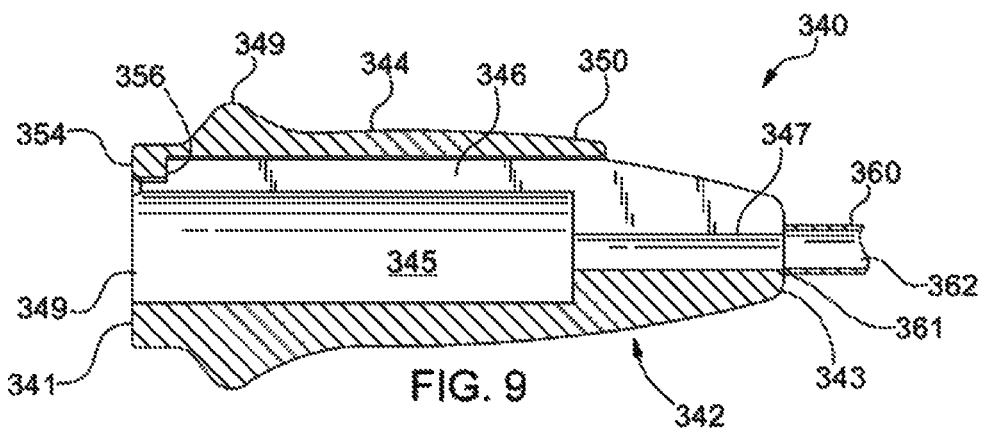
FIG. 9 is a cross-sectional view along the line 9-9 in FIG. 7.
Figure 10:
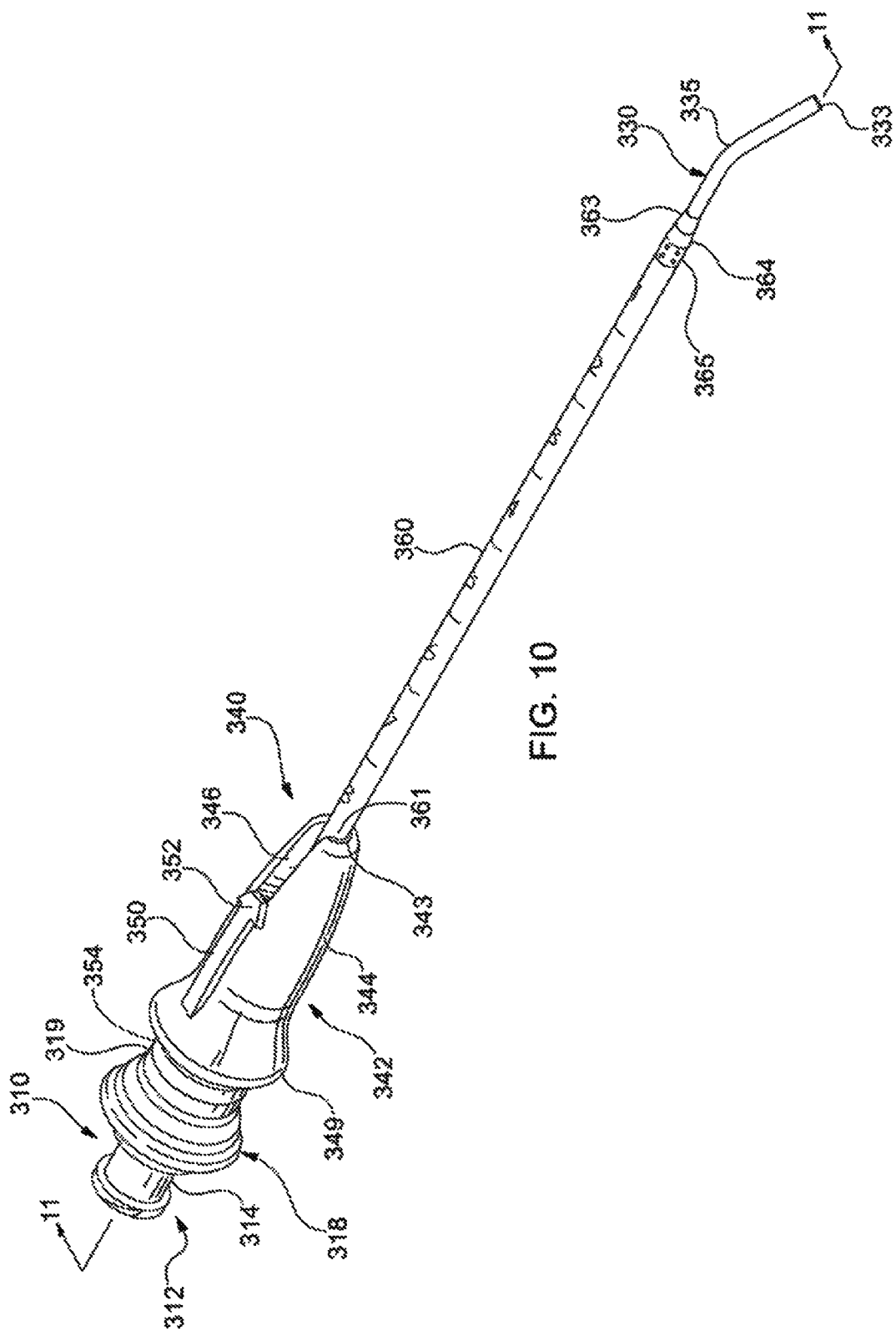
FIG. 10 is a perspective view similar to FIG. 2 illustrating the sphenocath in an extended position.

Referring to FIGS. 2-12, a sphenocath 300 in accordance with an exemplary embodiment of the invention will be described. The sphenocath 300 generally comprises a catheter assembly 310 and a sheath assembly 340. As explained in more detail below, the catheter assembly 310 is configured to be positioned within the sheath assembly 340 and to be moved between an initial, non-extended position as illustrated in FIG. 2 and an extended position as illustrated in FIG. 10.

Referring to FIGS. 4-6, the exemplary catheter assembly 310 generally includes a catheter tube 330 extending from a catheter hub 312. The catheter hub 312 has a generally cylindrical body 314 extending between a proximal end 311 and a distal end 313. A through passage 316 extends through the body 314 from the proximal end 311 to the distal end 313. The proximal end of the passage 316 may have a larger opening 315 which then tapers at 317 to the diameter of the lumen 332 of the catheter tube 330. The proximal end 311 of the catheter hub 312 preferably includes a thread 308 or the like for connection of the catheter assembly 310 to a syringe or the like (not shown). The distal end 313 of the catheter hub 312 includes a radial projection 322 configured to guide motion relative to the sheath hub 342 as described hereinafter. The radial projection 322 includes a proximal shoulder 321 and a distal tapered surface 323 which facilitates passage of the catheter hub 312 into the sheath hub 342. The projection 322 has a width was illustrated in FIG. 6.

Between the ends 311, 313, the catheter hub 312 includes one or more annular rings 318 which define a gripping structure of the catheter hub 312. A distal most ring 318 defines a stop 319 which limits the amount of distal movement of the catheter hub 312 relative to the sheath hub 342. The catheter hub 312 is preferably manufactured from a generally rigid material, for example, a polymer such as ISOPLAST 2510.

Figure 11:
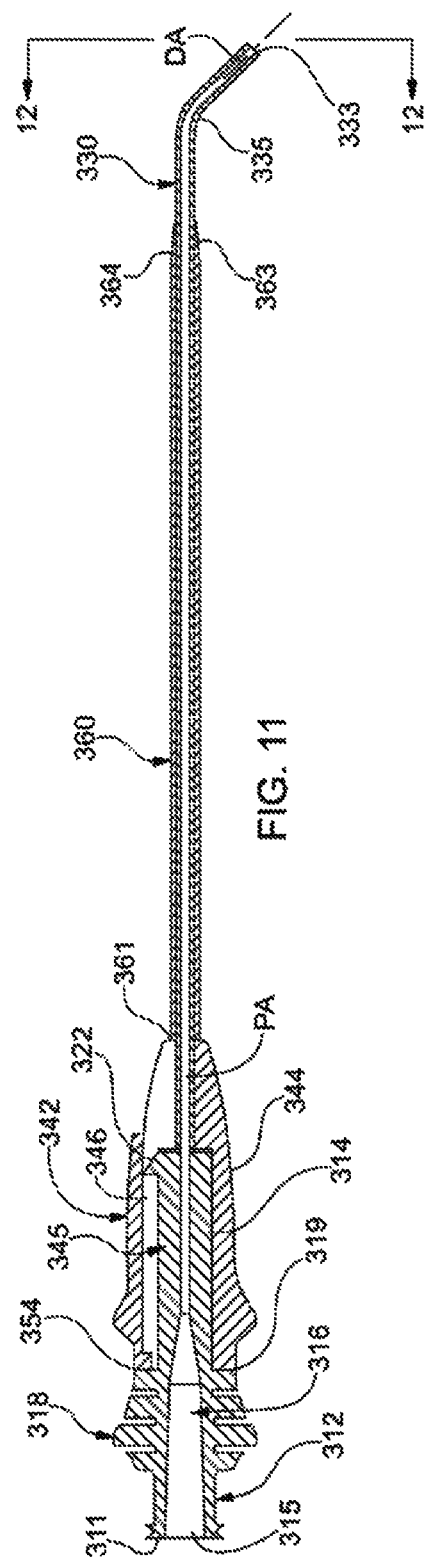
FIG. 11 is a cross-sectional view along the line 11-11 in FIG. 10.
Figure 12:
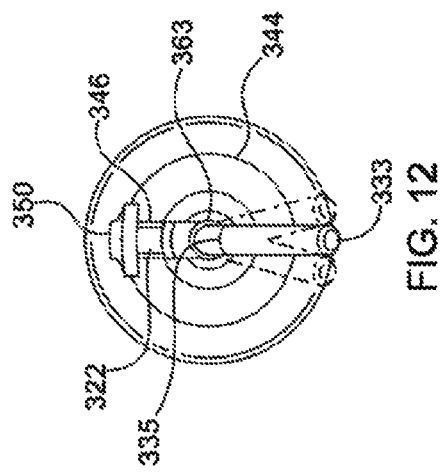
FIG. 12 is an elevation view along the line 12-12 in FIG. 10.

The catheter tube 330 extends from a proximal end 331 secured within the hub passage 316 to a free distal end 333. The catheter tube 330 is manufactured from a flexible material, for example, a polyurethane elastomer such as PELLETHANE. The catheter tube 330 defines a hollow lumen 332 extending from the proximal end 331 to the distal end 333 such that a continuous passage is defined by the catheter hub passage 316 and the lumen 332. Referring to FIGS. 10-12, the distal end 333 of the catheter tube 330 may be formed with a preformed curvature 335. The curvature 335 is such that an axis DA of the distal end 333 is at an angle relative to the axis PA of the proximal end 331. The angle is preferably between 30 degrees to 90 degrees and more preferably is between 35 degrees to 55 degrees. The angle is preferably chosen to correspond to the anatomy of the patient's nasal cavity.

Figure 7:
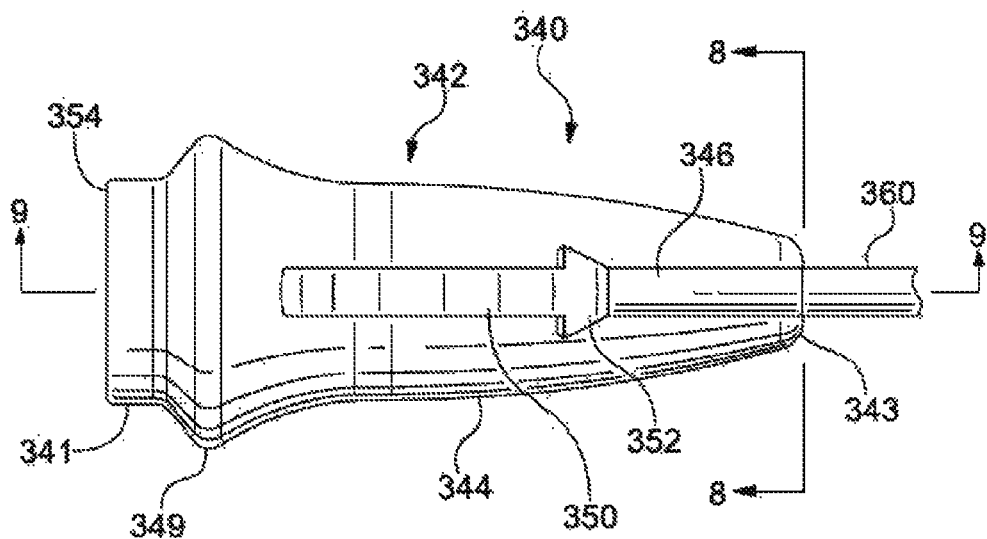
FIG. 7 is a top plan view of a portion of an exemplary sheath assembly of the sphenocath of FIG. 2.

Referring to FIGS. 7-9, the exemplary sheath assembly 340 will be described. The sheath assembly 340 generally includes a sheath tube 360 extending from a sheath hub 342. The sheath hub 342 has a generally tubular body 344 extending between a proximal end 341 and a distal end 343. A through passage 345 extends through the body 344 from the proximal end 341 to the distal end 343. The proximal end of the passage 345 may have a larger opening 349 while the distal end 343 has a smaller passage 347 which approximates the diameter of the lumen 362 of the sheath tube 360. The proximal end 341 of the catheter hub 342 preferably includes an annular shoulder 354 about the opening 349 which defines an internal shoulder 356.

Figure 14:
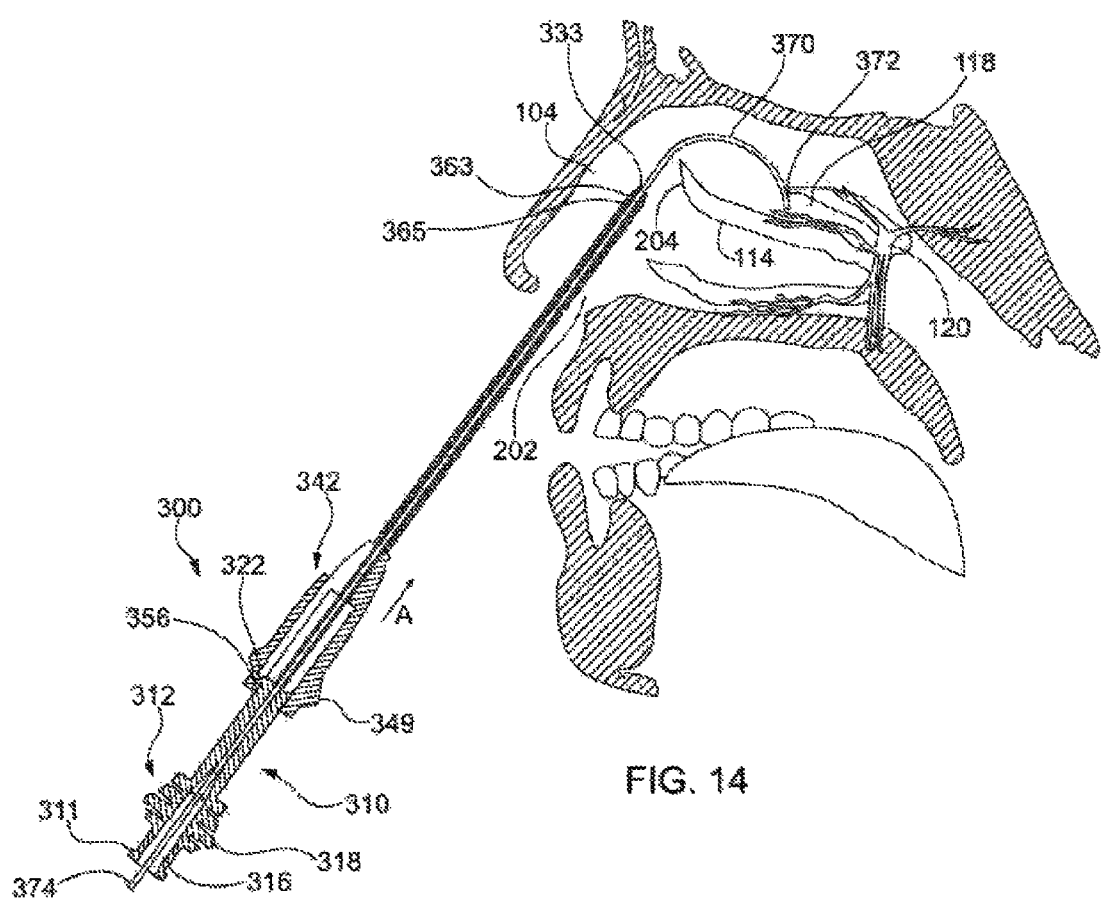
FIG. 14 illustrates the positioning of the sphenocath of FIG. 2 in the initial position as it is positioned along the guidewire.

A guide slot 346 extends along the top surface of the sheath hub body 344 from the shoulder 356 to the distal end 343. As illustrated in FIG. 8, the guide slot 346 has a width W which is slightly larger than the width w of the catheter hub projection 322. As illustrated in FIGS. 11 and 12, the distal end of the catheter hub 312 is received in the passage 345 such that the projection 322 moves within the guide slot 346. Referring to FIG. 14, contact of the projection proximal shoulder 321 with the internal shoulder 356 limits proximal movement of the catheter hub 312 relative to the sheath hub 342.

Positioning of the projection 322 in the guide slot 346 also controls the relative rotational movement between the hubs 312 and 342. As illustrated in FIG. 12, the larger width W of the guide slot 346 compared to the width w of the projection 322 allows for slight rotation of the catheter tube distal end 333 over a limited range, for example, approximately 10 degrees in each direction. In this way, the orientation of the preformed curvature 335 of the catheter tube distal end 333 cannot be modified relative to the sheath hub 342 beyond the controlled range.

Referring again to FIGS. 7-9, an indicator member 350 with an arrow head 352 covers a portion of the guide slot 346, preferably at least over the range of axial movement of the projection 322 within the slot 346. The indicator member 350 provides an indication of the orientation of the device 300 and more specifically the orientation of the preformed curvature 335. Since, as explained above, the engagement of the projection 322 in the guide slot 346 limits relative rotation between the hubs 312, 342, the preformed curvature 335 will always be away from the indicator member 350. As illustrated in FIGS. 2 and 9, the indicator member 350 may be formed with a curvature that mimics the preformed curvature 335, i.e. away from a user looking from above and proximally of the sheath hub 342.

The sheath tube 360 extends from a proximal end 361 secured to the sheath hub 342 to a free distal end 363. The sheath tube 360 defines a hollow lumen 362 extending from the proximal end 361 to the distal end 363 such that a continuous passage is defined by the sheath hub passage 345 and the lumen 362. The distal end 363 of the sheath tube 360 preferably has a tapered portion 364 which provides a tapered contact surface during advancement of the sheath tube 360 and also conforms the sheath tube diameter to that of the catheter tube 330 outer diameter. The outer surface of the sheath tube 360, preferably on the top surface, has a plurality of markers 366 which are spaced a given distance from one another. The markers 366 can be used to illustrate a depth of insertion of the device, for example, the defined depth being a depth equaling a distance between an entrance to a patient's sphenopalatine recess and an external entrance to the patient's nostril or a depth relative to a guidewire 370 over which the sphenocath 300 is guided as will be described hereinafter. The sheath tube 360 may also include a radiopaque mark 665 adjacent to the distal end 363 to assist with placement of the sphenocath 300 utilizing x-ray or fluoroscopy.

The sheath tube 360 is manufactured from a semi-flexible material that is more rigid than the catheter tube 330, but may still have some flexibility. In this way, the sheath tube 360 maintains the preformed curvature 335 straight while within the sheath tube 360. The sheath tube 360 may also be manufactured from, for example, a polyurethane elastomer such as PELLETHANE, however, it will be a composition that provides the greater rigidity. The sheath tube 360 may be formed with a lubricant blended with the material thereof or may be coated with a lubricant such that the sheath tube 360 has an external lubricious surface that minimizes the need for additional lubricants that may irritate the tracked area.

Figure 13:
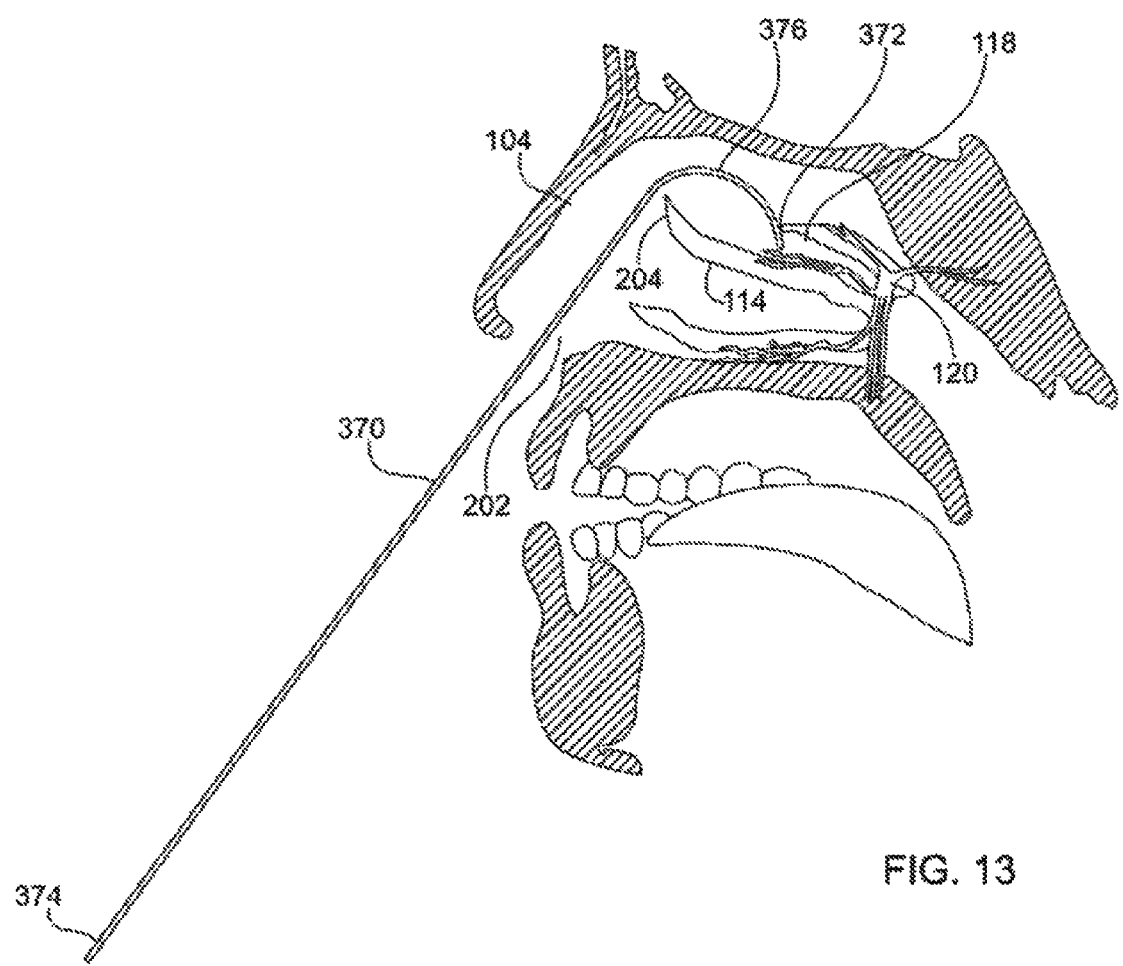
FIG. 13 illustrates the positioning of an exemplary guidewire within the nasal cavity of a patient.

Referring to FIG. 13, the system further includes a guidewire 370 over which the sphenocath 300 is guided. The guidewire 370 extends from a proximal end 374 to a distal end 372. The distal end 372 may be formed with a preformed curvature 376 which approximates the preformed curvature 335 of the catheter tube 330, however, it is understood that the curvatures may be different.

Having described the components of an exemplary system, an exemplary method of insertion of the catheter tube 330 into a patient's nasal cavity will be described with reference to FIGS. 13-15. First, the distal end 372 of the guidewire 370 is inserted into the nostril 202 as illustrated in FIG. 13. Such insertion may be done, for example, using fluoroscopic guidance or by physician feel into the sphenopalatine/pterygopalatine recess or targeted location to access.

Referring to FIG. 14, the proximal end 374 of the guidewire 370 is received into the catheter tube distal end 333 and the sphenocath 300 is advanced over the guidewire 370 as indicated by arrow A. It is noted that at this stage, the catheter hub 312 is in the initial, non-extended position and the distal end 333 of the catheter tube 330 is proximate to the distal end 363 of the sheath tube 360. The sphenocath 300 is advanced over the guidewire 370 to the desired position and location, for example, with the distal end 363 of the sheath tube 360 proximate the anterior ridge 204 of the middle sinus turbinate 114. As explained above, the markings 366 may be utilized to help with the depth of insertion and the radiopaque mark 665 may further assist with placement.

Figure 15:
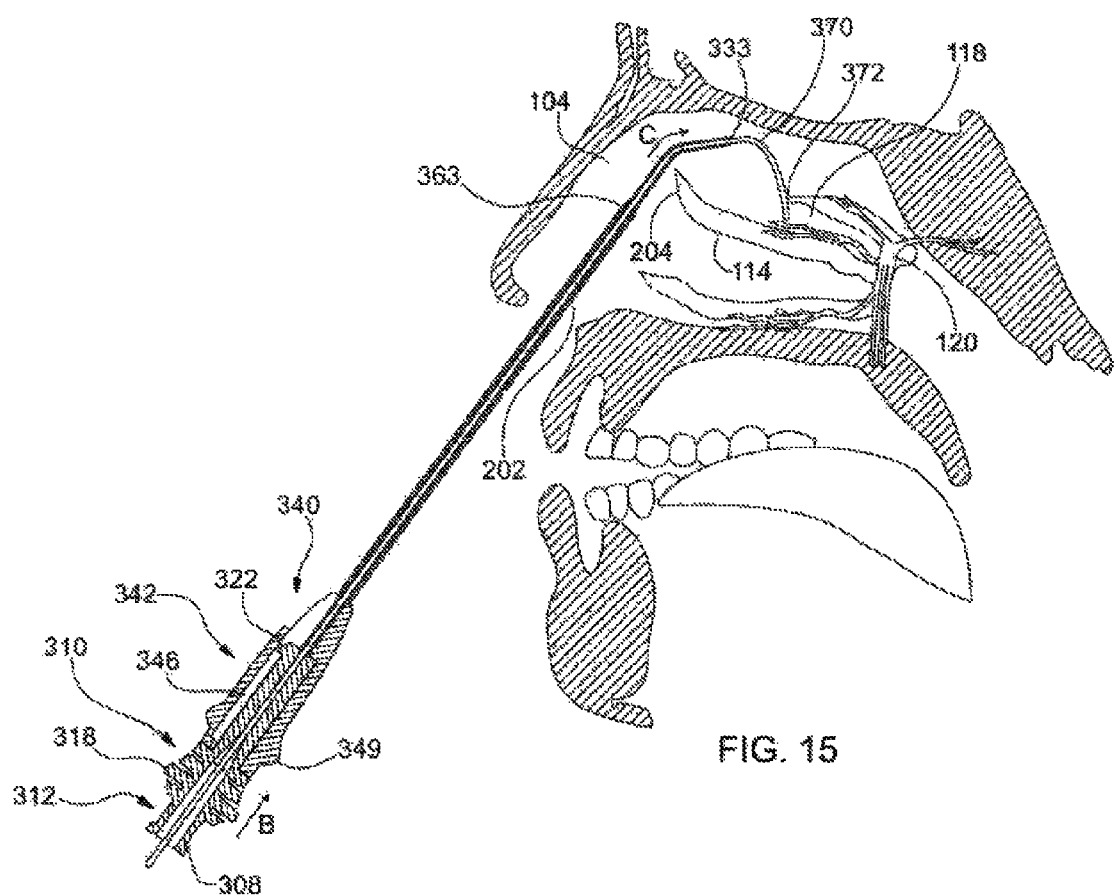
FIG. 15 illustrates extension of the catheter from the sheath with the patient's nasal cavity.

Referring to FIG. 15, the catheter hub 312 is then advanced distally relative to the sheath hub 342 as indicated by arrow B. As such, the distal end 333 of the catheter tube 330 is extended out of the distal end 363 of the sheath tube 360. The catheter tube distal end 333 follows the path defined by the guidewire distal end 372 as indicated by arrow C. The catheter distal end 333 is advanced into the patient's sphenopalatine/pterygopalatine recess 118 of the patient or another desired position.

Once the catheter distal end 333 is positioned, the guidewire 370 is removed and the catheter assembly 310 is ready for the desired application, with a passage defined from the hub passage 316 and through the lumen 332. For example, a syringe or the like (not shown) may be connected to the thread 308 and a fluid, for example, contrast media, or medication, may be dispensed to the patient's sphenopalatine/pterygopalatine ganglion 120 disposed within the sphenopalatine/pterygopalatine recess 118.

Figure 16:
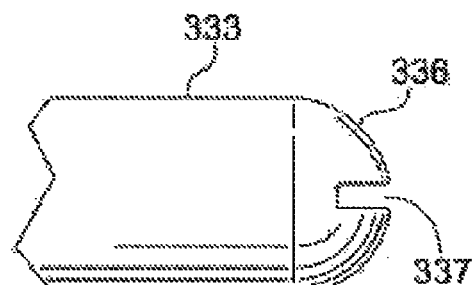
FIG. 16 is a side elevation view of an exemplary catheter distal end.
Figure 17:
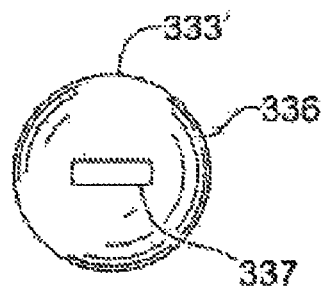
FIG. 17 is an end elevation view of the catheter distal end of FIG. 16.
Figure 18:
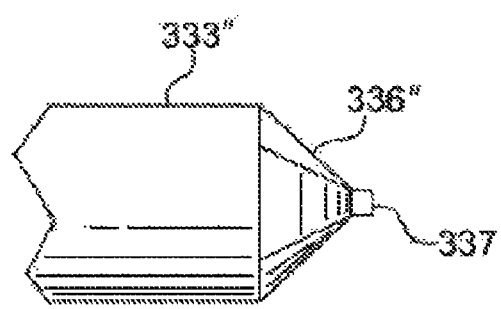
FIG. 18 is a side elevation view of another exemplary catheter distal end.
Figure 19:
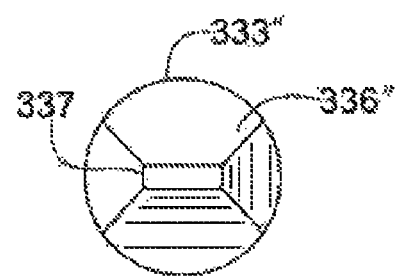
FIG. 19 is an end elevation view of the catheter distal end of FIG. 18.
Figure 20:
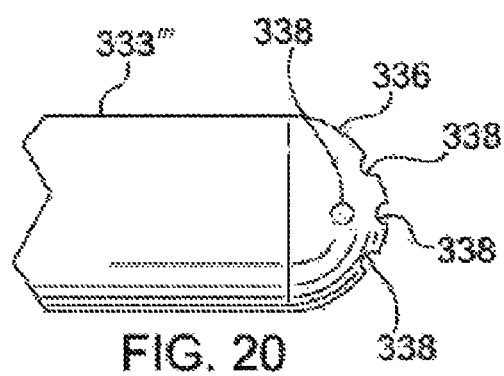
FIG. 20 is a side elevation view of another exemplary catheter distal end.
Figure 21:
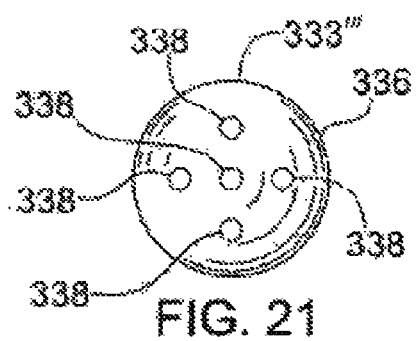
FIG. 21 is an end elevation view of the catheter distal end of FIG. 20.

Referring to FIGS. 16 and 17, the configuration of an exemplary catheter 310 distal end 333' will be described. The distal end 333' has a substantially closed end 336 except for a slotted passage 337 extending across the closed end 336. The slotted passage 337 will cause fluid expelled from the catheter 310 to fan out and provide a spraying or "painting" of the entire target area. FIGS. 18 and 19 illustrate another spraying tip wherein the catheter distal end 333" has a similar slotted passage 337, however, the closed end 336" tapers to the passage 337, rather than the rounded end in the previous embodiment. In both embodiments, the slotted passage 337 preferably extends horizontally relative to the angle of the catheter distal end 333. FIGS. 20 and 21 illustrate another spraying tip wherein the catheter distal end 333"' has a substantially closed end 336 except for a series of small openings 338. The openings 338 will again cause fluid expelled from the catheter 310 to fan out provide a spraying or "painting" of the entire target area. While five openings 338 are illustrated, more or fewer openings may be provided and may be arranged in configurations other than the illustrated configuration.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed:

1. A method for visualization and/or administration of medication of and into the sphenopalatine/pterygopalatine recess of a patient comprising:

inserting a guidewire into a nostril of a patient to a target area proximate the sphenopalatine/pterygopalatine recess of the patient;

providing a sphenocath including a sheath assembly having a sheath hub with a sheath tube extending therefrom with a passage extending from a proximal end of the sheath hub to a distal end of the sheath tube, said sheath hub including a guide slot extending along a top surface thereof, said guide slot including an indicator member covering a portion of said guide slot; a catheter assembly including a catheter hub with a catheter tube extending therefrom, a distal end of said catheter tube having a preformed curvature, the catheter tube having a passage extending from a proximal end of the catheter hub to a distal end of the catheter tube, said catheter hub including a radially extending projection thereon, wherein the indicator member indicates the orientation of the distal end of the catheter tube and wherein the catheter assembly is configured to pass through the sheath assembly such that the radially extending projection on the catheter hub engages the guide slot to limit relative rotation between the hubs over a limited rotational range, wherein the limited rotational range extends approximately 10 degrees in each rotational direction such that the preformed curvature is always away from the indicator member and the catheter tube distal end cannot be modified relative to the sheath hub beyond the limited range while permitting relative axial movement such that in an initial non-extended position the distal end of the catheter tube is proximate to the distal end of the sheath tube, wherein said guide slot has a width larger than a width of the projection such that the catheter hub is configured to rotate relative to the sheath hub over the limited rotational range;

advancing the sphenocath over the guidewire and rotating the catheter hub relative to the sheath hub to conform to an anatomy of the patient's sphenopalatine/pterygopalatine recess, such that the distal end of the catheter tube is proximal to the target area;

advancing the catheter assembly relative to the sheath assembly whereby the catheter tube distal end extends from the sheath tube distal end and bends along the guidewire;

visually confirming a direction of the preformed curvature and aligning the preformed curvature of the catheter tube distal end with the patient's sphenopalatine/pterygopalatine recess removing the guidewire; and dispensing contrast media, fluids, and/or medication to the patient's sphenopalatine/pterygopalatine ganglion disposed within the sphenopalatine recess of the patient.

2. The method of claim 1, wherein said contrast media, fluids, or medication is delivered over a middle sinus turbinate of the patient to achieve sphenopalatine ganglion blockade.

3. The method of claim 2, wherein sympathetic nerves of the patient are impacted by accessing the sphenopalatine recess at the back of a sinus cavity extending from a top of the middle sinus turbinate.

4. The method of claim 2, wherein the sphenopalatine ganglion blockade is not achieved by saturation of different areas within a sinus cavity or a throat of the patient.

5. The method of claim 1, wherein transnasal sphenopalatine visualization is achieved by delivery of contrast media over a middle sinus turbinate of the patient.

6. The method of claim 1, wherein the sheath tube distal end includes a radiopaque mark and the step of advancing the sphenocath over the guidewire includes the use of x-ray or fluoroscopy.

7. The method of claim 1, wherein the sheath tube includes a series of distance markings and the step of advancing the sphenocath over the guidewire includes advancement based on, at least in part, the distance markings.

* * * * *